(12) United States Patent
Watanabe et al.

(10) Patent No.: US 9,237,997 B2
(45) Date of Patent: Jan. 19, 2016

(54) COSMETIC PREPARATION CONTAINING CROSSLINKABLE SILICONE RUBBER EMULSION AND ITS PRODUCTION METHOD

(71) Applicant: Nissin Chemical Industry Co., Ltd., Echizen-shi, Fukui-ken (JP)

(72) Inventors: Kentaro Watanabe, Echizen (JP); Akira Yamamoto, Echizen (JP)

(73) Assignee: NISSIN CHEMICAL INDUSTRY CO., LTD., Echizen-shi (JP)

( * ) Notice: Subject to any disclaimer, the term of this patent is extended or adjusted under 35 U.S.C. 154(b) by 84 days.

(21) Appl. No.: 13/778,585

(22) Filed: Feb. 27, 2013

(65) Prior Publication Data
US 2013/0225698 A1 Aug. 29, 2013

(30) Foreign Application Priority Data
Feb. 29, 2012 (JP) ................................. 2012-043952

(51) Int. Cl.
| | |
|---|---|
| A61K 8/891 | (2006.01) |
| A61Q 19/00 | (2006.01) |
| A61K 8/898 | (2006.01) |
| A61K 8/06 | (2006.01) |
| C08G 77/16 | (2006.01) |
| C08L 83/04 | (2006.01) |
| C08G 77/00 | (2006.01) |

(52) U.S. Cl.
CPC ............. *A61K 8/891* (2013.01); *A61K 8/066* (2013.01); *A61K 8/898* (2013.01); *A61Q 19/00* (2013.01); *C08G 77/16* (2013.01); *C08G 77/80* (2013.01); *C08L 83/04* (2013.01); *C08L 2201/52* (2013.01)

(58) Field of Classification Search
None
See application file for complete search history.

(56) References Cited

U.S. PATENT DOCUMENTS

| | | | |
|---|---|---|---|
| 3,294,725 A | 12/1966 | Findlay et al. | |
| 5,633,303 A | 5/1997 | Kondo et al. | |
| 5,928,660 A | 7/1999 | Kobayashi et al. | |
| 6,150,425 A * | 11/2000 | Sekine et al. | 516/22 |
| 7,658,972 B2 | 2/2010 | Matsumura et al. | |
| 2003/0225236 A1* | 12/2003 | Takahashi et al. | 528/12 |
| 2006/0121300 A1* | 6/2006 | Matsumura | 428/541 |
| 2007/0042124 A1* | 2/2007 | Matsumura et al. | 427/440 |
| 2012/0276037 A1 | 11/2012 | Suzuki et al. | |

FOREIGN PATENT DOCUMENTS

| | | |
|---|---|---|
| JP | 8-245881 A | 9/1996 |
| JP | 10-175816 A | 6/1998 |
| JP | 11-071522 A | 3/1999 |
| JP | 2007-051236 A | 3/2007 |
| WO | WO 02/088253 A | 11/2002 |
| WO | WO 2011/064974 A1 | 6/2011 |

OTHER PUBLICATIONS

Extended European Search Report dated Sep. 9, 2014, for European Application No. 13156850.3.

* cited by examiner

*Primary Examiner* — Ernst V Arnold
*Assistant Examiner* — Jianfeng Song
(74) *Attorney, Agent, or Firm* — Birch, Stewart, Kolasch & Birch, LLP

(57) ABSTRACT

A cosmetic preparation containing a crosslinkable silicone rubber emulsion comprising (A) 100 parts by weight of a straight chain or branched organopolysiloxane containing at least two hydroxyl groups bonded to the silicon atom per molecule prepared by ring-opening polymerization of a cyclic organosiloxane in the presence of an alkoxysilane or its partial hydrolytic condensate or an α,ω-dihydroxy or dialkoxy siloxane oligomer by using a catalyst selected from citric, lactic, and ascorbic acids and an anionic surfactant emulsifier; and (B) 0.5 to 20 parts by weight of a reaction product of an amino group-containing organoxysilane and an acid anhydride.

5 Claims, No Drawings

COSMETIC PREPARATION CONTAINING CROSSLINKABLE SILICONE RUBBER EMULSION AND ITS PRODUCTION METHOD

CROSS-REFERENCE TO RELATED APPLICATION

This non-provisional application claims priority under 35 U.S.C. §119(a) on Patent Application No. 2012-043952 filed in Japan on Feb. 29, 2012, the entire contents of which are hereby incorporated by reference.

TECHNICAL FIELD

This invention relates to a cosmetic preparation containing a crosslinkable silicone rubber emulsion which can be produced by a simple method, and which exhibits lower skin irritancy. This invention also proposes its production method.

BACKGROUND ART

Aqueous emulsion of a silicone rubber resin has been known in the art, and various products are on the market including those intended for the cosmetic preparation. However, almost all such commercially available products for the application of cosmetic preparation are silicone rubber resins emulsified and dispersed in water by using a silicone oil or the like, and these products can not be regarded as a product in an aqueous system. JP-A H10-175816 discloses the system wherein silicone rubber particles are synthesized, dried, and again emulsified and dispersed, and this process requires the steps of drying and emulsification in addition to the step of the polymerization. Another known products are aqueous dispersions of the silicone rubber by addition reaction of a hydrogen polysiloxane and a vinyl polysiloxane. These products, however, tend to undergo separation, and because of such separation, almost all of these aqueous dispersions were used in the form of powder after separation and they were rarely used in the cosmetic preparation in the form of an aqueous dispersion. In another method, the silicone rubber produced, for example, by solution polymerization is dissolved again in a silicone oil, and then subjected to mechanical emulsification (JP-A H08-245881). This method is economically disadvantageous.

Silicone emulsions capable of forming a film by crosslinking have also been disclosed in JP-A 2007-51236, and these products are in the market since their high strength and softness as well as water repellency were highly evaluated. These are products prepared by simple emulsion polymerization using a siloxane for the starting material, and thus economically advantageous. These products, however, contained surfactants and acids unsuitable for cosmetic products.

JP-A H11-71522 discloses a polyorganosiloxane emulsion prepared by emulsion polymerization of a silanol group-endcapped polydiorganosiloxane in the presence of (B) an unsaturated aliphatic sulfonate and/or sulfonate methyl hydroxide formed in the reaction system of a sulfonate salt and an acid and (C) water. This polyorganosiloxane emulsion, however, uses sulfuric acid, hydrochloric acid, formic acid, and sulfonic acid in its production. These acids are mostly strong acids under the restriction of Poisonous and Deleterious Substances Control Act and other laws, and their use in the application of cosmetic preparation is unsuitable. Formic acid which is not a strong acid is also under the restriction of Poisonous and Deleterious Substances Control Act as a deleterious substance when used at a high concentration, and its use in the application of cosmetic preparation is also unsuitable.

JP-B S44-20116 discloses an emulsion polymerization method of an organosiloxane and a silanol group-containing disilcarbane in an aqueous medium in the presence of a sulfonic acid catalyst having surfactant activity selected from benzene sulfonic acid substituted with an aliphatic hydrocarbon group, naphthalene sulfonic acid, aliphatic hydrocarbon sulfonic acid, and silylalkylsulfonic acid, which is most typically an alkylbenzene sulfonic acid such as dodecylbenzene sulfonic acid. However, these are silicone oils, and they are used in a manner clearly different from the silicone rubber. As in the case of literatures as described above, the acid used is a strong acid which is unsuitable for use in the application of cosmetic preparation.

Such polymerization also inevitably involves use of an anionic surfactant such as sodium laurylsulfate or sodium laureth sulfate. However, these compounds, are irritant and under the restriction of Law concerning Pollutant Release and Transfer Register (hereinafter also referred to as PRTR). Also, these compounds may be toxic to human and environment (aquatic life), and accordingly, they are not suitable as a material used in cosmetic preparations.

In addition, properties such as high spreadability, lighter texture, and softer touch are expected for a preparation used in cosmetic applications.

SUMMARY OF INVENTION

Technical Problem

The present invention has been completed in view of the situation as described above, and an object of the present invention is to provide a cosmetic preparation containing a crosslinkable silicone rubber emulsion which has been prepared by solely using ingredients which are not under the restriction of Poisonous and Deleterious Substances Control Act and Law concerning Pollutant Release and Transfer Register and which are not hard on the skin, and which exhibits performance equivalent to commercial silicone rubber emulsions, and which is in the form usable for the application of cosmetic preparations. Another object of the present invention is to provide its production method.

Solution to Problem

In order to achieve the objects as described above, the inventors of the present invention made an intensive investigation and found that, a straight chain or branched organopolysiloxane prepared by ring-opening polymerization using a cyclic organosiloxane for the main starting material, citric acid, lactic acid, or ascorbic acid for the catalyst, and an anionic surfactant, and in particular, an N-acylamino acid salt, an N-acyltaurinate, an aliphatic soap, or an alkylphosphate salt for the emulsifier is suitable as an organopolysiloxane for use in a cosmetic preparation; and that a mixture of such organopolysiloxane with the reaction product of an amino group-containing organoxysilane and an acid anhydride is effective as a component of a cosmetic preparation. The present invention has been completed on the bases of such findings.

Accordingly, the present invention provides a cosmetic preparation and its production method as described below.

[1] A cosmetic preparation containing a crosslinkable silicone rubber emulsion comprising (A) 100 parts by weight of a straight chain or branched organopolysiloxane containing at least two hydroxyl groups bonded to silicon atoms per molecule prepared by ring-opening polymerization of a cyclic organosiloxane in the presence of an alkoxysilane or its partial hydrolytic condensate or an α,ω-dihydroxy or dialkoxy siloxane oligomer by using at least one member selected from citric acid, lactic acid, and ascorbic acid as a catalyst and using an anionic surfactant as an emulsifier; and (B) 0.5 to 20 parts by weight of a reaction product of an amino group-containing organoxysilane and an acid anhydride.

[2] A cosmetic preparation according to [1] wherein the straight chain or branched organopolysiloxane of component (A) is represented by the following general formula (1):

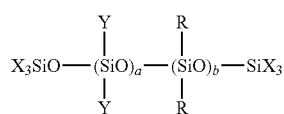
(1)

wherein R is independently an alkyl group containing 1 to 20 carbon atoms or an aryl group containing 6 to 20 carbon atoms; X is independently an alkyl group containing 1 to 20 carbon atoms, an aryl group containing 6 to 20 carbon atoms, an alkoxy group containing 1 to 20 carbon atoms, or hydroxyl group; Y is independently X or a group represented by —[O—Si(X)$_2$]$_c$—X, at least 2 of X and Y being hydroxyl group; letter a is an integer of 0 to 1,000; letter b is an integer of 100 to 10,000; and letter c is an integer of 1 to 1,000; with the proviso that each constitutional repeating unit may be randomly bonded.

[3] A cosmetic preparation according to [1] or [2] wherein the amino group-containing organoxysilane of component (B) is the one represented by the following general formula (2):

wherein R is independently an alkyl group containing 1 to 20 carbon atoms or an aryl group containing 6 to 20 carbon atoms, A is an amino-containing group represented by the formula: —R$^1$(NHR$^1$)$_h$NHR$^2$ wherein R$^1$ is independently a divalent hydrocarbon group containing 1 to 6 carbon atoms, R$^2$ is R or hydrogen atom, and letter h is an integer of 0 to 6, and letter g is 0, 1, or 2, and the acid anhydride is a dicarboxylic acid anhydride.

[4] A cosmetic preparation according to any one of [1] to [3] wherein the catalyst for obtaining the component (A) is citric acid.

[5] A cosmetic preparation according to any one of [1] to [4] wherein the anionic surfactant for obtaining the component (A) is at least one member selected from N-acylamino acid salt, N-acyltaurinate, aliphatic soap, and alkylphosphate salt.

[6] A cosmetic preparation according to any one of [1] to [5] which is for low-irritant skin care.

[7] A method for producing a cosmetic preparation comprising the steps of
producing a crosslinkable silicone rubber emulsion comprising a straight chain or branched organopolysiloxane (A) containing at least two hydroxyl groups bonded to silicon atoms per molecule prepared by ring-opening polymerization of a cyclic organosiloxane preferably at a temperature of 55 to 85° C., more preferably at a temperature of 65 to 75° C. in the presence of an alkoxysilane or its partial hydrolytic condensate or an α,ω-dihydroxy or dialkoxy siloxane oligomer by using at least one member selected from citric acid, lactic acid, and ascorbic acid as a catalyst and using an anionic surfactant as an emulsifier; and mixing the silicon rubber emulsion with a reaction product (B) of an amino group-containing organoxysilane and an acid anhydride at a mixing ratio of 0.5 to 20 parts by weight of the component (B) in relation to 100 parts by weight of the organopolysiloxane (A).

[8] A method for producing a cosmetic preparation according to [7] wherein the straight chain or branched organopolysiloxane of component (A) is represented by the following general formula (1):

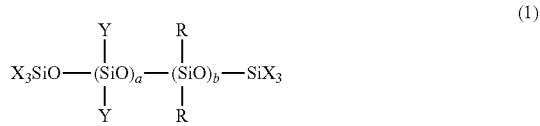
(1)

wherein R is independently an alkyl group containing 1 to 20 carbon atoms or an aryl group containing 6 to 20 carbon atoms; X is independently an alkyl group containing 1 to 20 carbon atoms, an aryl group containing 6 to 20 carbon atoms, an alkoxy group containing 1 to 20 carbon atoms, or hydroxyl group; Y is independently X or a group represented by —[O—Si(X)$_2$]$_c$—X, at least 2 of X and Y being hydroxyl group; letter a is an integer of 0 to 1,000; letter b is an integer of 100 to 10,000; and letter c is an integer of 1 to 1,000; with the proviso that each constitutional repeating unit may be randomly bonded.

[9] A method for producing a cosmetic preparation according to [7] or [8] wherein the amino group-containing organoxysilane of component (B) is the one represented by the following general formula (2):

wherein R is independently an alkyl group containing 1 to 20 carbon atoms or an aryl group containing 6 to 20 carbon atoms, A is an amino-containing group represented by the formula:
—R$^1$(NHR$^1$)$_h$NHR$^2$ wherein R$^1$ is independently a divalent hydrocarbon group containing 1 to 6 carbon atoms, R$^2$ is R or hydrogen atom, and letter h is an integer of 0 to 6, and letter g is 0, 1, or 2, and the acid anhydride is a dicarboxylic acid anhydride.

[10] A method for producing a cosmetic preparation according to any one of [7] to [9] wherein the catalyst for obtaining the component (A) is citric acid.

[11] A method for producing a cosmetic preparation according to any one of [7] to [10] wherein the catalyst for obtaining the component (A) is used in an amount of 0.01 to 10 parts by weight in relation to 100 parts by weight of the cyclic organosiloxane.

[12] A method for producing a cosmetic preparation according to any one of [7] to [11] wherein the anionic surfactant for obtaining the component (A) is at least one member selected from N-acylamino acid salt, N-acyltaurinate, aliphatic soap, and alkylphosphate salt, and the anionic surfactant is used in an amount of 0.1 to 20 parts by weight in relation to 100 parts by weight of the cyclic organosiloxane.

Advantageous Effects of Invention

The crosslinkable silicone rubber emulsion used in the cosmetic preparation of the present invention exhibits performance comparable to the conventional silicone rubber emulsions while it is prepared from ingredients which are not under the restriction of Poisonous and Deleterious Substances Control Act and Law concerning Pollutant Release and Transfer Register and which are not hard on the skin. Due to the use of such silicone rubber emulsion, the cosmetic preparation has reduced environmental burden, less irritancy to the skin, higher water resistance, and higher comfortability in use.

DESCRIPTION OF EMBODIMENTS

The cosmetic preparation of the present invention contains a silicone rubber emulsion comprising (A) 100 parts by weight of a straight chain or branched organopolysiloxane containing at least two hydroxyl groups bonded to the silicon atom per molecule prepared by ring-opening polymerization of a cyclic organosiloxane in the presence of an alkoxysilane or its partial hydrolytic condensate or an α,ω-dihydroxy or dialkoxy siloxane oligomer by using at least one member selected from citric acid, lactic acid, and ascorbic acid as a catalyst and using an anionic surfactant as an emulsifier; and (B) 0.5 to 20 parts by weight of a reaction product of an amino group-containing organoxysilane and an acid anhydride.

The organopolysiloxane of the component (A) contains at least 2 hydroxy groups bonded to the silicon atom per molecule, and this organopolysiloxane is preferably a straight chain or branched organopolysiloxane represented by the following general formula (1):

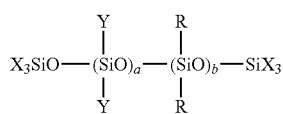

wherein R is independently an alkyl group containing 1 to 20 carbon atoms or an aryl group containing 6 to 20 carbon atoms; X is independently an alkyl group containing 1 to 20 carbon atoms, an aryl group containing 6 to 20 carbon atoms, an alkoxy group containing 1 to 20 carbon atoms, or hydroxyl group; Y is independently X or a group represented by —[O—Si(X)$_2$]$_c$—X, at least 2 of X and Y being hydroxyl group; letter a is an integer of 0 to 1,000; letter b is an integer of 100 to 10,000; and letter c is an integer of 1 to 1,000; with the proviso that each constitutional repeating unit may be randomly bonded.

In the formula, R is independently an alkyl group containing 1 to 20 carbon atoms or an aryl group containing 6 to 20 carbon atoms. Examples of the R include methyl, ethyl, propyl, butyl, pentyl, hexyl, heptyl, octyl, nonyl, decyl, dodecyl, tetradecyl, hexadecyl, octadecyl, cyclopentyl, cyclohexyl, cycloheptyl, phenyl, tolyl, and naphthyl groups, and the preferred is methyl group.

X is independently an alkyl group containing 1 to 20 carbon atoms, an aryl group containing 6 to 20 carbon atoms, an alkoxy group containing 1 to 20 carbon atoms, or hydroxyl group, and examples include hydroxyl group, and groups such as methyl, ethyl, propyl, butyl, pentyl, hexyl, heptyl, octyl, nonyl, decyl, dodecyl, tetradecyl, hexadecyl, octadecyl, cyclopentyl, cyclohexyl, cycloheptyl, phenyl, tolyl, naphthyl, methoxy, ethoxy, propoxy, butoxy, hexyloxy, heptyloxy, octyloxy, decyloxy, and tetradecyloxy groups.

Y is independently X or a group represented by —[O—Si(X)$_2$]$_c$—X.

Letter a is an integer of 0 to 1,000, and preferably 0 to 200 since the integer in excess of 1,000 will result in the insufficient strength of the resulting film. Letter b is an integer of 100 to 10,000, and preferably 1,000 to 5,000 since the integer of less than 100 will result in the poor softness of the resulting film while the integer in excess of 10,000 will invite loss of film tear strength. Letter c is an integer of 1 to 1,000.

In view of the crosslinkability, at least 2, and preferably 2 to 4 hydroxyl groups are present per molecule preferably at opposite ends.

Exemplary organopolysiloxanes include:

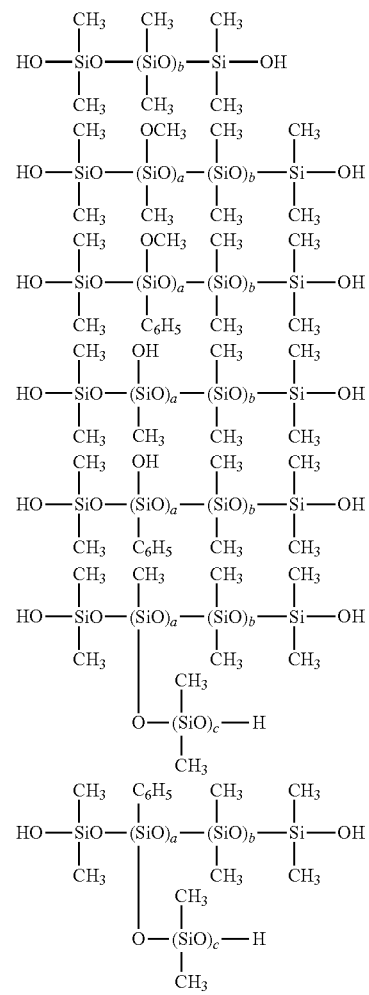

wherein a, b, and c are as defined above.

The straight chain or branched organopolysiloxane is obtained by using a cyclic organosiloxane for its main ingredient, and also using an alkoxysilane or its partial hydrolytic condensate or α,ω-dihydroxy or dialkoxy siloxane oligomer. The most preferred is alkoxysilane.

In this case, exemplary cyclic organosiloxanes include: hexamethylcyclotrisiloxane (D3), octamethylcyclotetrasiloxane (D4), decamethylcyclopentasiloxane (D5), dodecamethylcyclohexasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris(3,3,3- trifluoropropyl)trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, and 1,3,5,7-tetra(N-acryloyl-N-methyl-3-aminopropyl)tetramethylcyclotetrasiloxane, 1,3,5,7-tetra(N,N-bis(lauroyl)-3-aminopropyl)tetramethylcyclotetrasiloxane, namely, D3 to D20 representing the number of cyclic dimethylsiloxane unit (D: molecular formula, $SiO(CH_3)_2$).

The preferred is a cyclic siloxane represented by $[SiO(CH_3)_2]_n$, wherein n is an integer of 3 to 10.

The more preferred are octamethylcyclotetrasiloxane, and decamethylcyclopentasiloxane.

Exemplary alkoxysilanes include methyltrimethoxysilane, methyltriethoxysilane, methyltripropoxysilane, methyltributhoxysilane, ethyltrimethoxysilane, ethyltriethoxysilane, propyltrimethoxysilane, propyltriethoxysilane, butyltrimethoxysilane, pentyltrimethoxysilane, hexyltrimethoxysilane, octyltrimethoxysilane, decyltrimethoxysilane, dodecyltrimethoxysilane, tetradecyltrimethoxysilane, octadecyltrimethoxysilane, vinyltrimethoxysilane, vinyltriethoxysilane, phenyltrimethoxysilane, phenyltriethoxysilane, 3,3,3-trifluoropropyltrimethoxysilane, 3,3,3-trifluoropropyltriethoxysilane, tetramethoxy silane, tetraethoxysilane, tetrapropoxysilane, and tetrabuthoxysilane.

Among these, the preferred are methyltrimethoxysilane, methyltriethoxysilane, phenyltrimethoxysilane, phenyltriethoxysilane, vinyltrimethoxysilane, vinyltriethoxysilane, 3,3,3-trifluoropropyltrimethoxysilane, 3,3,3-trifluoropropyltriethoxy silane, tetramethoxysilane, and tetraethoxysilane.

The alkoxysilane or its partial hydrolytic condensate or an α,ω-dihydroxy or dialkoxy siloxane oligomer is preferably used in an amount of 0.01 to 5 parts by weight, more preferably 0.01 to 2 parts by weight, and still more preferably 0.01 to 1 part by weight in relation to 100 parts by weight of the cyclic organosiloxane.

In the present invention, the organopolysiloxane of the formula (1) is obtained from the starting materials as described above by ring opening polyperization by using at least one member selected from citric acid, lactic acid, and ascorbic acid for the catalyst, and an anionic surfactant for the emulsifier.

The anionic surfactant is preferably the one listed in Japanese Standards of Quasi-drug Ingredients (JSQI) 2006 and the one not restricted by The Japanese Standards of Cosmetic Ingredients in the Pharmaceutical Affairs Law, and the one which is less irritant, and the one not restricted by poisonous or deleterious substance in the Poisonous and Deleterious Substances Control Act, or Law concerning Pollutant Release and Transfer Register (PRTR).

Examples of such anionic surfactants include N-acylamino acid salts, N-acyltaurinates, aliphatic soaps, and alkylphosphate salts, and the preferred are those which are highly soluble in water and those not having polyethylene oxide chain. The anionic surfactant is more preferably selected from N-acylamino salts, N-acyltaurinates, aliphatic soaps, and alkylphosphate salts, especially N-acylamino acid salts in which the acyl group has 10 to 20 carbon atoms, N-acyltaurinates in which the acyl group has 10 to 20 carbon atoms, aliphatic soaps having 10 to 20 carbon atoms, and alkylphosphate salts having 10 to 20 carbon atoms. The preferred salt is an alkali metal salt. Sodium lauroyl methyltaurate or sodium myristoyl methyltaurate is most preferred.

Preferably, 0.1 to 20 parts by weight, and more preferably 0.5 to 10 parts by weight of the anionic surfactant is used in relation to the 100 parts by weight of the cyclic organosiloxane. When the content is excessively low, the emulsification will not proceed or the emulsification will be extremely unstable, while excessively high content may lead to insufficient reaction of the cyclic organosiloxane.

A nonionic surfactant such as polyoxyethylene alkylether may be used in combination with the anionic surfactant. However, use of nonionic surfactant alone can not retain its surfactant activity under the high temperature, acidic conditions of the polymerization.

The acid catalyst used for the polymerization catalyst is preferably the one not restricted by The Japanese Standards of Cosmetic Ingredients in the Pharmaceutical Affairs Law, and the one listed in Japanese Standards of Quasi-drug Ingredients 2006, and the one not restricted by poisonous or deleterious substance in the Poisonous and Deleterious Substances Control Act, or Law concerning Pollutant Release and Transfer Register. Examples include citric acid, lactic acid, and ascorbic acid, and the preferred is citric acid.

Preferably, 0.01 to 10 parts by weight, and more preferably 0.2 to 2 parts by weight of the catalyst is used in relation to 100 parts by weight of the cyclic organosiloxane. Use of an excessively low amount may result in the insufficient reaction while use of too much catalyst results in the larger amount of the alkali required for neutralization, and this may lead to decrease of the solid content in the system or instability of the emulsion due to the increase metal ion.

As described above, conventional catalysts such as dodecylbenzenesulfonic acid, hydrochloric acid, and sulfuric acid are not preferable for use in the present invention. The catalyst used in the present invention is preferably the one wherein the skin irritancy as described below is up to 10.

In this case, even if the strong acid conventionally used is substituted with a weak acid such as acetic acid or butyric acid, unreacted material may be left or the resulting product may have a small molecular weight, failing to obtain a product having necessary property.

By using ascorbic acid, citric acid or lactic acid and adjusting the polymerization temperature, the polymerization time and the amount of acid, there can be obtained good cosmetic material.

When the emulsion polymerization is conducted by using the ingredients as described above, the amount of the water is preferably 50 to 200 parts by weight in relation to 100 parts by weight of cyclic organosiloxane.

In the present invention, the polymerization as described above may be conducted by the method and conditions known in the art. When the catalyst used is a weak acid in the polymerization, higher temperature tends to result in the higher degree of polymerization. In the present invention, the temperature preferably used in the polymerization is 55 to 85° C., more preferably 65 to 75° C. The polymerization time is properly selected although it is preferably about 1 to 40 hours. Too low polymerization temperature such as room temperature may not cause the ring opening or may insufficiently cause the ring opening. Too high polymerization temperature may not keep the stability of the emulsion.

In the present invention, the straight chain or branched organopolysiloxane is obtained in the form of an emulsion, and the resulting emulsion may be used either without further dilution or concentration, or with dilution or concentration to a solid concentration of 20 to 50% by weight, and in particular, 30 to 50% by weight.

The mixing of the reaction product of an amino group-containing organoxysilane and an acid anhydride (the component (B)) with the organopolysiloxane (the component (A)) and the drying results in the formation of a cured silicone which has undergone three dimensional crosslinking. Preferably, the reaction product is the amino group-containing alkoxysilane and the dicarboxylic anhydride, and in the present invention, the amino group-containing organoxysilane is preferably an ethoxy group-containing silane in view of the cosmetic purpose.

The starting amino group-containing organoxysilane is the one represented by the following general formula (2):

$$A(R)_g Si(OR)_{3-g} \qquad (2)$$

wherein R is as defined above, A is an amino-containing group represented by the formula —$R^1(NHR^1)_h NHR^2$ wherein $R^1$ is independently a divalent hydrocarbon group such as an alkylene group containing 1 to 6 carbon atoms. Examples of $R^1$ include methylene, ethylene, propylene, butylene, or hexylene group. $R^2$ is R or hydrogen atom, and h is an integer of 0 to 6, preferably 0 or 1, and g is 0, 1, or 2. Examples include:

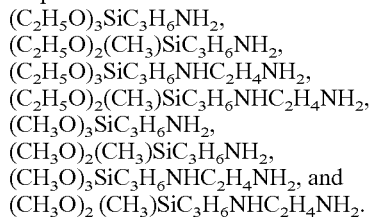

$(C_2H_5O)_3SiC_3H_6NH_2$,
$(C_2H_5O)_2(CH_3)SiC_3H_6NH_2$,
$(C_2H_5O)_3SiC_3H_6NHC_2H_4NH_2$,
$(C_2H_5O)_2(CH_3)SiC_3H_6NHC_2H_4NH_2$,
$(CH_3O)_3SiC_3H_6NH_2$,
$(CH_3O)_2(CH_3)SiC_3H_6NH_2$,
$(CH_3O)_3SiC_3H_6NHC_2H_4NH_2$, and
$(CH_3O)_2(CH_3)SiC_3H_6NHC_2H_4NH_2$.

Since the alcohol generated is preferably ethanol, the OR group is most preferably ethoxy group.

The acid anhydride added for reaction with the amino group-containing organoxysilane is preferably a dicarboxylic anhydride, and the one preferable for cosmetic purpose is succinic anhydride.

Amount of the acid anhydride reacted is preferably 10 to 60 parts by weight, and more preferably 40 to 60 parts by weight in relation to 100 parts by weight of the amino group-containing organoxysilane. Excessively low amount of the acid anhydride may result in low rubber property, and excessive amount may result in the yellowing of the reaction product.

The reaction process between the amino group-containing organoxysilane and the acid anhydride may be readily accomplished at room temperature or under heated conditions and, if desired, in a hydrophilic organic solvent depending on the blend ratio of these components. Exemplary hydrophilic organic solvent used in this reaction include alcohols such as methanol, ethanol, isopropanol, and butanol, ketones such as acetone and methyl ethyl ketone, acetonitrile, and tetrahydrofuran. The hydrophilic organic solvent may be used in an amount of about 0 to 100% by weight of the reaction product.

The reaction temperature is not particularly limited as long as the temperature is at least room temperature, and the reaction temperature is preferably 20 to 100° C. The reaction time is not particularly limited, and the reaction time is preferably 1 to 4 hours.

When the reaction between the amino group-containing organoxysilane and the acid anhydride is conducted by using a hydrophilic organic solvent, the component (B) may be used either with or without removal of the solvent.

The solid content (namely, the reaction product between the amino group-containing organoxysilane and the acid anhydride) in the reaction product is preferably in the range of 10 to 40% by weight and more preferably about 20 to 30% by weight. Elastomeric property will be insufficient when the solid content is too low, while excessively high content invites instability of the emulsion.

Amount of the reaction product (B) of the amino group-containing organoxysilane and the acid anhydride is 0.5 to 20 parts by weight, and preferably 1 to 10 parts by weight in relation to 100 parts by weight of the organopolysiloxane (A) containing at least two hydroxyl groups bonded to the silicon atom per molecule. Excessively low content of the component (B) results in poor rubber property while excessively high content results in the instability of the emulsion and hard texture.

Mixing of the components (A) and (B) by a method known in the art using, for example, a stirrer, propeller agitator, or the like results in the formation of a crosslinkable silicone rubber emulsion emulsified and dispersed in water. The mixing may be conducted for 5 to 30 minutes, and preferably, at a temperature of 10 to 30° C. As described above, mixing and curing of the component (A) and the component (B) results in the formation of a cured silicone which has undergone the three dimensional crosslinking.

The solid content in the silicone rubber emulsion is preferably about 20 to 50% by weight, and more preferably 30 to 50% by weight.

The resulting silicone rubber emulsion may preferably have a viscosity as measured by a B viscometer of 10 to 5,000 mPa·s, and more preferably 50 to 1,000 mPa·s.

For use of the silicone rubber emulsion in producing a cosmetic preparation, the intrinsic viscosity as measured by an Ubbelohde viscometer is preferably 0.1 to 0.9 mm²/s, and more preferably 0.3 to 0.9 mm²/s so that the skin does not feel difference in rubber texture.

In this case, the viscosity can be adjusted by the addition of carboxyvinyl polymer, polyacrylic acid, or acrylic acid-acrylate copolymer.

With regard to the average particle diameter measured by a laser diffraction particle size distribution analyzer, the silicone rubber emulsion may have an average particle diameter of preferably up to 1 μm, and more preferably 100 to 300 nm.

The pH of the silicone rubber emulsion is preferably in the range of 6 to 8.

As described above, silicone emulsions have been used in the form of powder due to insufficiency in the storage stability, separation, and the like of the conventional silicone emulsions. In contrast, the silicone rubber emulsion of the present invention has high storage stability with on separation even after 1 month.

The resulting silicone rubber emulsion is capable of forming a rubber film, and this film may be imparted with water repellency, steam permeability, comfortability, and the like, and also, with water resistance by crosslinking. Because of the reduced skin irritancy, the silicone rubber emulsion is highly expected for use in cosmetic applications such as hair-care preparations, skin-care preparations, make-up preparations, body-care preparations, sun screen, and in particular, for skin-care applications.

The crosslinkable silicone rubber emulsion is preferably incorporated at a solid content of 5 to 50% by weight of the entire cosmetic preparation. Sufficient effect may not be realized when the content is less than 5% by weight, while content in excess of 50% by weight may result in excessive rubber property unsuitable for cosmetic application. For example, Example 1 as described below is a mixture of 223 parts by weight (100 parts by weight of solid content) of the emulsion of Preparation Example 1, 10 parts by weight (5 parts by weight of solid content) of the solution of Preparation Example 11, 200 parts by weight of isohexadecane, and 200 parts by weight of KF-6105 (manufactured by Shin-Etsu Chemical Co., Ltd. polyglycerin-modified silicone oil). Accordingly, content crosslinkable silicone rubber emulsion is 105/633=16.5% by weight.

The cosmetic preparation may also include an oily ingredient, solvent, powder, and the like in addition to the crosslinkable silicone rubber emulsion invention.

Exemplary oily ingredients include hydrocarbons, silicone oils, triglycerides, ester oils, fats, waxes, higher fatty acids, and higher alcohols, and the particularly preferred are low boiling point silicone oil, low boiling point isoparaffin hydrocarbon, and triglycerides, and ester oils.

The content of the oily ingredient in the cosmetic preparation is properly selected from the type of the cosmetic preparation and is such an amount that the effect of the cosmetic preparation is not harmed, although the oily ingredient is preferably incorporated in an amount of 0.1 to 95% by weight, more preferably 1 to 80% by weight in the cosmetic preparation. If the amount is less than 0.1% by weight, the effect of the oily ingredient such as slippery property and moisture property may not be exerted. If the amount is more than 95% by weight, the stability may become inferior.

Exemplary solvents include lower to semi-higher alcohols and aromatic alcohols, and use of a lower alcohol such as isopropyl alcohol is preferable.

The content of the solvent in the cosmetic preparation is properly selected from the type of the cosmetic preparation and is such an amount that the effect of the cosmetic preparation, although the solvent is preferably incorporated in an amount of 0.1 to 80% by weight, more preferably 1 to 50% by weight in the cosmetic preparation.

The powder is not particularly limited as long as it can be used in normal make up preparation. Exemplary powders include colorants such as an inorganic color pigment, inorganic white pigment, and organic pigment, a pearl agent, an extender pigment, and organic powders. If desired in particular application, a powder having the surface covered with an oily ingredient such as silicone may also be used.

The content of the powder is properly selected from the type of the cosmetic preparation and is such an amount that the effect of the cosmetic preparation is not harmed, although the powder is preferably incorporated in an amount of 0.1 to 95% by weight, more preferably 0.1 to 50% by weight, most preferably 0.5 to 40% by weight in the cosmetic preparation.

The method of incorporating the above ingredients may be properly selected. For example, the crosslinkable silicone rubber emulsion is simply mixed with the other suitable ingredients homogenously. Alternatively, the other suitable ingredients are preliminarily emulsified with an emulsifier such as homogenizer, colloid mill or line mixer or preliminarily mixed homogenously, and the crosslinkable silicone rubber emulsion is added and dispersed therein.

In addition to the components as described above, the cosmetic preparation of the present invention may further comprise a surfactant, oily ingredient, macromolecular compound, gelation agent, alkaline agent, polyhydric alcohol, pH adjusting agent, UV absorbent, antioxidant, antiseptic, antiphlogistic, skin care component, flavor, and other components commonly incorporated in a cosmetic preparation suitable for the application of the preparation at a quantitative and qualitative range not adversely affecting the merits of the crosslinkable silicone rubber emulsion of the present invention.

Exemplary cosmetic preparations of the present invention include make up preparations such as foundation, white powder, eye shadow, eye liner, eye blow pencil, cheek blusher, lip stick, and nail color; base cosmetic preparations such as milky lotion, cream, lotion, calamine lotion, sunscreen, sun tan lotion, aftershave lotion, pre-shave lotion, pack preparations, antiacne preparation, and essence; hair cosmetic preparations such as shampoo, rinse, conditioner, hair color, hair tonic, setting agent, hair restorer agent, and hair permanent agent; body powder, deodorant preparation, depilatory, soap, body shampoo, bath agent, hand soap, and perfume. The crosslinkable silicone rubber emulsion of the present invention is less irritant to the skin, and therefore, its use for skin-care preparations such as base cosmetic preparations is preferable.

EXAMPLES

Next, the present invention is described in further detail by referring to Preparation Examples, Examples, and Comparative Examples which by no means limit the scope of the present invention. In the following Examples, "parts" and "%" are respectively "parts by weight" and "% by weight".

Component (A)

Comparative Preparation Example 1

A solution of 498 g of octamethylcyclotetrasiloxane, 2 g of triethoxyphenylsilane, and 5 g of sodium lauryl sulfate in 45 g of pure water, and a solution of 5 g of dodecylbenzene sulfonic acid in 45 g of pure water were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 50° C. for 24 hours. After aging at 10° C. for 24 hours, 12 g of 10% aqueous solution of sodium carbonate was added for neutralization until the pH was 6.2. This emulsion had an involatile content after drying at 105° C. for 3 hours of 45.4%, and the organopolysiloxane in the emulsion was in the state of an unflowable soft gel having an average composition of $[(CH_3)SiO_{2/2}]/[(C_6H_5)SiO_{3/2}]$ of 100/0.1 (molar ratio) with its terminal capped with hydroxy group. An emulsion [Comparative Preparation Example 1] was thereby obtained.

Comparative Preparation Example 2

A solution of 498 g of octamethylcyclotetrasiloxane, 2 g of phenyltriethoxysilane, and 5 g of sodium lauryl sulfate in 45 g of pure water, and a solution of 14 g of 35% hydrochloric acid in 36 g of water were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 50° C. for 24 hours. After aging at 10° C. for 24 hours, 12 g of 10% aqueous solution of sodium carbonate was added for neutralization until the pH was 6.2. This emulsion had an involatile content after drying at 105° C. for 3 hours of 44.2%, and the organopolysiloxane in the emulsion was in the state of an unflowable soft gel having an average composition of $[(CH_3)_2SiO_{2/2}]/[(C_6H_5)SiO_{3/2}]$ of 100/0.1 (molar ratio) with its terminal capped with hydroxy group. An emulsion [Comparative Preparation Example 2] was thereby obtained.

Comparative Preparation Example 3

A solution of 498 g of octamethylcyclotetrasiloxane, 2 g of phenyltriethoxysilane, and 5 g of sodium lauryl sulfate in 45 g of pure water, and 2 g of butyric acid were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 50° C. for 24 hours. After aging at 10° C. for 24 hours, 12 g of 10% aqueous solution of sodium carbonate was added for neutralization until the pH was 6.2. This emulsion had an involatile content after drying at 105° C. for 3 hours of 41.0%, and the organopolysiloxane in the emulsion was in the state of an unflowable soft gel having an average composition of $[(CH_3)_2SiO_{2/2}]/[(C_6H_5)SiO_{3/2}]$ of 100/0.1 (molar ratio) with its terminal capped with hydroxy group. An emulsion [Comparative Preparation Example 3] was thereby obtained.

Comparative Preparation Example 4

A solution of 498 g of octamethylcyclotetrasiloxane, 2 g of phenyltriethoxysilane, and 5 g of sodium lauryl sulfate in 45 g of pure water, and 2 g of acetic acid were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 50° C. for 24 hours. After aging at 10° C. for 24 hours, 12 g of 10% aqueous solution of sodium carbonate was added for neutralization until the pH was 6.2. This emulsion had an involatile content after drying at 105° C. for 3 hours of 40.8%, and the organopolysiloxane in the emulsion was in the state of an unflowable soft gel having an average composition of $[(CH_3)_2SiO_{2/2}]/[(C_6H_5)SiO_{3/2}]$ of 100/0.1 (molar ratio) with its terminal capped with hydroxy group. An emulsion [Comparative Preparation Example 4] was thereby obtained.

Preparation Example 1

A solution of 498 g of octamethylcyclotetrasiloxane, 2 g of phenyltriethoxysilane, and 5 g of sodium lauroyl methyltaurate in 95 g of pure water, and a solution of 3.8 g of citric acid were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 70° C. for 24 hours. After aging at 10° C. for 24 hours, 42 g of 10% aqueous solution of sodium carbonate was added for neutralization until the pH was 6.2. This emulsion had an involatile content after drying at 105° C. for 3 hours of 44.8%, and the organopolysiloxane in the emulsion was in the state of an unflowable soft gel having an average composition of $[(CH_3)_2SiO_{2/2}]/[(C_6H_5)SiO_{3/2}]$ of 100/0.1 (molar ratio) with its terminal capped with hydroxy group. An emulsion [Preparation Example 1] was thereby obtained.

Preparation Example 2

A solution of 498 g of octamethylcyclotetrasiloxane, 2 g of phenyltriethoxysilane, and 5 g of sodium lauroyl methyltaurate in 95 g of pure water, and a solution of 1.9 g of citric acid were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 70° C. for 24 hours. After aging at 10° C. for 24 hours, 24 g of 10% aqueous solution of sodium carbonate was added for neutralization until the pH was 6.2. This emulsion had an involatile content after drying at 105° C. for 3 hours of 44.7%, and the organopolysiloxane in the emulsion was in the state of an unflowable soft gel having an average composition of $[(CH_3)_2SiO_{2/2}]/[(C_6H_5)SiO_{3/2}]$ of 100/0.1 (molar ratio) with its terminal capped with hydroxy group. An emulsion [Preparation Example 2] was thereby obtained.

Preparation Example 3

A solution of 498 g of octamethylcyclotetrasiloxane, 2 g of phenyltriethoxysilane, and 10 g of sodium myristoyl methyltaurate in 90 g of pure water, and a solution of 3.8 g of citric acid were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 70° C. for 24 hours. After aging at 10° C. for 24 hours, 42 g of 10% aqueous solution of sodium carbonate was added for neutralization until the pH was 6.2. This emulsion had an involatile content after drying at 105° C. for 3 hours of 44.5%, and the organopolysiloxane in the emulsion was in the state of an unflowable soft gel having an average composition of $[(CH_3)_2SiO_{2/2}]/[(C_6H_5)SiO_{3/2}]$ of 100/0.1 (molar ratio) with its terminal capped with hydroxy group. An emulsion [Preparation Example 3] was thereby obtained.

Preparation Example 4

A solution of 498 g of octamethylcyclotetrasiloxane, 2 g of phenyltriethoxysilane, and 10 g of sodium lauroyl methyltaurate in 90 g of pure water, and a solution of 3.8 g of citric acid were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 70° C. for 24 hours. After aging at 10° C. for 24 hours, 45 g of 10% aqueous solution of sodium carbonate was added for neutralization until the pH was 6.2. This emulsion had an involatile content after drying at 105° C. for 3 hours of 45.0%, and the organopolysiloxane in the emulsion was in the state of an unflowable soft gel having an average composition of $[(CH_3)_2SiO_{2/2}]/[(C_6H_5)SiO_{3/2}]$ of 100/0.1 (molar ratio) with its terminal capped with hydroxy group. An emulsion [Preparation Example 4] was thereby obtained.

Preparation Example 5

A solution of 498 g of octamethylcyclotetrasiloxane, 2 g of phenyltriethoxysilane, and 5 g of sodium lauroyl methyltaurate in 95 g of pure water, and a solution of 7.6 g of citric acid were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 70° C. for 24 hours. After aging at 10° C. for 24 hours, 60 g of 10% aqueous solution of sodium carbonate was added for neutralization until the pH was 6.2. This emulsion had an involatile content after drying at 105° C. for 3 hours of 42.7%, and the organopolysiloxane in the emulsion was in the state of an unflowable soft gel having an average composition of [(CH$_3$)$_2$SiO$_{2/2}$]/[(C$_6$H$_5$)SiO$_{3/2}$] of 100/0.1 (molar ratio) with its terminal capped with hydroxy group. An emulsion [Preparation Example 5] was thereby obtained.

Preparation Example 6

A solution of 498 g of octamethylcyclotetrasiloxane, 2 g of phenyltriethoxysilane, and 25 g of sodium lauroyl methyltaurate in 75 g of pure water, and a solution of 3.8 g of citric acid were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 70° C. for 24 hours. After aging at 10° C. for 24 hours, 45 g of 10% aqueous solution of sodium carbonate was added for neutralization until the pH was 6.2. This emulsion had an involatile content after drying at 105° C. for 3 hours of 45.2%, and the organopolysiloxane in the emulsion was in the state of an unflowable soft gel having an average composition of [(CH$_3$)$_2$SiO$_{2/2}$]/[(C$_6$H$_5$)SiO$_{3/2}$] of 100/0.1 (molar ratio) with its terminal capped with hydroxy group. An emulsion [Preparation Example 6] was thereby obtained.

Preparation Example 7

A solution of 498 g of octamethylcyclotetrasiloxane, 2 g of phenyltriethoxysilane, and 10 g of sodium lauroyl methyltaurate in 75 g of pure water, and a solution of 7.6 g of lactic acid were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 70° C. for 24 hours. After aging at 10° C. for 24 hours, 30 g of 10% aqueous solution of sodium carbonate was added for neutralization until the pH was 6.2. This emulsion had an involatile content after drying at 105° C. for 3 hours of 44.8%, and the organopolysiloxane in the emulsion was in the state of an unflowable soft gel having an average composition of [(CH$_3$)$_2$SiO$_{2/2}$]/[(C$_6$H$_5$)SiO$_{3/2}$] of 100/0.1 (molar ratio) with its terminal capped with hydroxy group. An emulsion composition [Preparation Example 7] was thereby obtained.

Preparation Example 8

A solution of 498 g of octamethylcyclotetrasiloxane, 2 g of phenyltriethoxysilane, and 10 g of sodium lauroyl methyltaurate in 75 g of pure water, and a solution of 10 g of L-ascorbic acid were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 70° C. for 24 hours. After aging at 10° C. for 24 hours, 45 g of 10% aqueous solution of sodium carbonate was added for neutralization until the pH was 6.2. This emulsion had an involatile content after drying at 105° C. for 3 hours of 44.7%, and the organopolysiloxane in the emulsion was in the state of an unflowable soft gel having an average composition of [(CH$_3$)$_2$SiO$_{2/2}$]/[(C$_6$H$_5$)SiO$_{3/2}$] of 100/0.1 (molar ratio) with its terminal capped with hydroxy group. An emulsion composition [Preparation Example 8] was thereby obtained.

Preparation Example 9

A solution of 498 g of octamethylcyclotetrasiloxane, 2 g of methyltriethoxysilane, and 10 g of sodium lauroyl methyltaurate in 75 g of pure water, and a solution of 3.8 g of citric acid were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 70° C. for 24 hours. After aging at 10° C. for 24 hours, 45 g of 10% aqueous solution of sodium carbonate was added for neutralization until the pH was 6.2. This emulsion had an involatile content after drying at 105° C. for 3 hours of 44.7%, and the organopolysiloxane in the emulsion was in the state of an unflowable soft gel having an average composition of [(CH$_3$)$_2$SiO$_{2/2}$]/[(C$_6$H$_5$)SiO$_{3/2}$] of 100/0.1 (molar ratio) with its terminal capped with hydroxy group. An emulsion composition [Preparation Example 9] was thereby obtained.

Preparation Example 10

A solution of 498 g of octamethylcyclotetrasiloxane, 2 g of methyltriethoxysilane, and 5 g of sodium lauroyl methyltaurate in 75 g of pure water, and a solution of 3.8 g of citric acid were charged in a 2 L polyethylene beaker, and the mixture was emulsified by using a homomixer. The emulsion was diluted by gradually adding 400 g of water to the emulsion, and then, passed twice through a high pressure homogenizer at a pressure of 300 kgf/cm$^2$ to thereby obtain a homogeneous white emulsion. This emulsion was transferred to a 2 L glass flask equipped with a stirrer, thermometer, and reflux condenser, and allowed to polymerize at 70° C. for 24 hours. After aging at 10° C. for 24 hours, 45 g of 10% aqueous solution of sodium carbonate was added for neutralization until the pH was 6.2. This emulsion had an involatile content after drying at 105° C. for 3 hours of 43.2%, and the organopolysiloxane in the emulsion was in the state of an unflowable soft gel having an average composition of [(CH$_3$)$_2$SiO$_{2/2}$]/[(C$_6$H$_5$)SiO$_{3/2}$] of 100/0.1 (molar ratio) with its terminal capped with hydroxy group. An emulsion composition [Preparation Example 10] was thereby obtained.

[Analysis]

The resulting emulsions were evaluated for their evaluation residue, viscosity, average particle diameter, intrinsic viscosity, storage stability by the procedure as described below. The results of the evaporation residue, viscosity, average particle diameter, and intrinsic viscosity are shown in Table 1.

Measurement of Evaporation Residue

About 1 g of the sample was weighed and placed on an aluminum foil dish, and heated in a dryer kept at 105 to 110° C. After heating for 1 hour, the sample was removed from the dryer and allowed to cool in a desiccator. The sample after drying was weighed and the evaporation residue was calculated by the following equation:

$$R = \frac{T-L}{W-L} \times 100$$

R: evaporation residue (%)
W: weight (g) of the aluminum foil dish and the sample before the drying
L: weight (g) of the aluminum foil dish g of the silicone resin. After discarding IPA, the remaining rubbery silicone resin was dried overnight at 60° C., and measured for its viscosity at 25° C. by using Ubbelohde viscometer. Intrinsic viscosity was calculated from the measurement time (specific viscosity of the toluene is 0.65, and the intrinsic viscosity is calculated from this value). See the following equation.

(1) toluene solution of dimethylpolysiloxane at a concentration of 1 g/100 mL was prepared to determine the specific viscosity ηsp at 25° C.

$$\eta sp = (\eta/\eta 0) - 1$$

*η0: viscosity of toluene, 1: viscosity of the solution
(2) Next, lisp is substituted in the relational equation of Huggins to calculate intrinsic viscosity [η].

$$\eta sp = [\eta] + K'[\eta]^2$$

*K': Huggins constant K'=0.3
(applicable when [η]=1 to 3)
[Reference] Nakamuta, Journal of the Chemical Society of Japan, 77 858 [1956]

The intrinsic viscosity is preferably in the range of 0.3 to 0.9 mm$^2$/s.

Storage Stability

Storage stability after storing at room temperature for 1 month was confirmed. Change in viscosity and particle diameter was also confirmed. Separation or other changes were not found in all of Preparation Examples, and no change was also found for the viscosity and the particle size: Sufficient long term stability was thereby confirmed.

TABLE 1

| | Comparative Preparation Example | | | | Preparation Example | | | | | | | | | |
|---|---|---|---|---|---|---|---|---|---|---|---|---|---|---|
| | 1 | 2 | 3 | 4 | 1 | 2 | 3 | 4 | 5 | 6 | 7 | 8 | 9 | 10 |
| Evaporation residue (%) | 45.1 | 44.2 | 41.0 | 40.8 | 44.8 | 44.7 | 44.5 | 45.0 | 42.7 | 45.2 | 44.8 | 44.7 | 44.7 | 43.2 |
| Viscosity (mPa·s) | 100 | 100 | 20 | 30 | 30 | 130 | 100 | 100 | 50 | 200 | 100 | 150 | 150 | 100 |
| Average particle diameter (nm) | 200 | 200 | 200 | 200 | 300 | 300 | 200 | 200 | 200 | 150 | 200 | 200 | 200 | 200 |
| Intrinsic viscosity (mm$^2$/s) | 0.82 | 0.85 | 0.34 | 0.30 | 0.75 | 0.36 | 0.48 | 0.78 | 0.77 | 0.68 | 0.32 | 0.28 | 0.72 | 0.38 |

T: weight (g) of the aluminum foil dish and the sample after the drying
Size of the aluminum foil dish: diameter 70 mm, height 12 mm Measurement of Viscosity using B Viscometer The sample solution was kept at 23±0.5° C., and the viscosity was measured by BM viscometer (No. 1 rotor, 6 rpm).

Measurement of Average Particle Diameter 0.01 g of the sample was weighed and evaluated for average particle diameter (the value of the particle diameter corresponding to 50% of the particle size cumulative distribution) using a laser diffraction particle size distribution analyzer (product name, LA-950V2 manufactured by Horiba) to measure under the circulation flow rate 2 and agitation speed 2.

Measurement Conditions
 Measurement temperature: 25±1° C.
 Solvent: ion exchanged water
Measurement of Intrinsic Viscosity 20 g of the emulsion was mixed with 20 g of IPA (isopropylalcohol) to break the emulsion to thereby obtain about 4.5

Component (B)

Preparation Example 11

154 g of succinic anhydride was dissolved in 500 g ethanol, and 346 g of 3-aminopropyltriethoxysilane was added to the solution at room temperature for 1 hour, and the reaction was allowed to proceed at 80° C. for 24 hours by refluxing the ethanol to obtain a pale yellow transparent solution [B-1] containing 50% of the component (B). This solution had an involatile content after drying at 105° C. for 3 hours of 45.1%. In the instrumental analysis of IR, GC, NMR, GCMS, and the like, about 60% was mixture of those represented by the following formulae and the remaining about 40% was oligomers derived therefrom.

(C$_2$H$_5$O)$_3$SiC$_3$H$_6$—NHCO—CH$_2$CH$_2$COOH

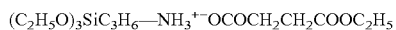
(C$_2$H$_5$O)$_3$SiC$_3$H$_6$—NH$_3^+$ $^-$OCOCH$_2$CH$_2$COOC$_2$H$_5$

Preparation Example 12

190 g of succinic anhydride was dissolved in 550 g ethanol, and 346 g of 3-aminopropyltriethoxysilane was added to the solution at room temperature for 1 hour, and the reaction was allowed to proceed at 80° C. for 24 hours by refluxing the ethanol to obtain a pale yellow transparent solution [B-2] containing 50% of the component (B). This solution had an involatile content after drying at 105° C. for 3 hours of 44.1%. In the instrumental analysis of IR, GC, NMR, GCMS, and the like, about 60% was mixture of those represented by the following formulae and the remaining about 40% was oligomers derived therefrom.

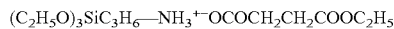

Comparative Example 1

10 parts (solid content, 5 parts) of the solution of the Preparation Example 11 was mixed with 222 parts (solid content, 100 parts) of the emulsion obtained in Comparative Preparation Example 1. After stirring the mixture at room temperature for about 10 minutes with a stirrer, the mixture was filtered by a 80 mesh filter, and 200 parts of isohexadecane and 200 parts of KF-6105 manufactured by Shin-Etsu Chemical Co., Ltd. were added to the filtrate. The mixture was agitated at room temperature for 10 minutes with an agitator to thereby obtain an O/W/O emulsion cream [Comparative Example 1].

Comparative Example 2

40 parts (solid content, 20 parts) of the solution of the Preparation Example 11 was mixed with 222 parts (solid content, 100 parts) of the emulsion obtained in Comparative Preparation Example 1, and the procedure of Comparative Example 1 was repeated to thereby obtain an O/W/O emulsion cream [Comparative Example 2].

Comparative Example 3

200 parts of isohexadecane and 200 parts of KF-6105 manufactured by Shin-Etsu Chemical Co., Ltd. were mixed with 167 parts of KM-903 manufactured by Shin-Etsu Chemical Co., Ltd. (solid content, 100 parts). The mixture was agitated with an agitator to obtain an O/W/O emulsion cream [Comparative Example 3].

Comparative Example 4

200 parts of isohexadecane and 200 parts of KF-6105 manufactured by Shin-Etsu Chemical Co., Ltd. were mixed with 167 parts of KM-910 manufactured by Shin-Etsu Chemical Co., Ltd. (solid content, 100 parts). The mixture was agitated with an agitator to obtain an O/W/O emulsion cream [Comparative Example 4].

Comparative Example 5

200 parts of isohexadecane and 200 parts of KF-6105 manufactured by Shin-Etsu Chemical Co., Ltd. were mixed with 226 parts of the emulsion obtained in Comparative Preparation Example 2. The mixture was agitated with an agitator to obtain an O/W/O emulsion cream [Comparative Example 5].

Comparative Example 6

10 parts (solid content, 5 parts) of the solution of the Preparation Example 11 was mixed with 224 parts (solid content, 100 parts) of the emulsion obtained in Comparative Preparation Example 3, and the procedure of Comparative Example 1 was repeated to thereby obtain an O/W/O emulsion cream [Comparative Example 6].

Comparative Example 7

10 parts (solid content, 5 parts) of the solution of the Preparation Example 11 was mixed with 245 parts (solid content, 100 parts) of the emulsion obtained in Comparative Preparation Example 4, and the procedure of Comparative Example 1 was repeated to thereby obtain an O/W/O emulsion cream [Comparative Example 7].

Example 1

10 parts (solid content, 5 parts) of the solution of the Preparation Example 11 was mixed with 223 parts (solid content, 100 parts) of the emulsion obtained in Preparation Example 1, and the procedure of Comparative Example 1 was repeated for emulsification and dispersion in water to thereby obtain an O/W/O emulsion cream [Example 1].

Example 2

10 parts (solid content, 5 parts) of the solution of the Preparation Example 11 was mixed with 224 parts (solid content, 100 parts) of the emulsion obtained in Preparation Example 2, and the procedure of Comparative Example 1 was repeated to thereby obtain an O/W/O emulsion cream [Example 2].

Example 3

10 parts (solid content, 5 parts) of the solution of the Preparation Example 11 was mixed with 225 parts (solid content, 100 parts) of the emulsion obtained in Preparation Example 3, and the procedure of Comparative Example 1 was repeated to thereby obtain an O/W/O emulsion cream [Example 3].

Example 4

40 parts (solid content, 20 parts) of the solution of the Preparation Example 11 was mixed with 223 parts (solid content, 100 parts) of the emulsion obtained in Preparation Example 1, and the procedure of Comparative Example 1 was repeated to thereby obtain an O/W/O emulsion cream [Example 4].

Example 5

10 parts (solid content, 5 parts) of the solution of the Preparation Example 11 was mixed with 222 parts (solid content, 100 parts) of the emulsion obtained in Preparation Example 4, and the procedure of Comparative Example 1 was repeated to thereby obtain an O/W/O emulsion cream [Example 5].

Example 6

10 parts (solid content, 5 parts) of the solution of the Preparation Example 11 was mixed with 234 parts (solid content, 100 parts) of the emulsion obtained in Preparation Example 5, and the procedure of Comparative Example 1 was repeated to thereby obtain an O/W/O emulsion cream [Example 6].

Example 7

10 parts (solid content, 5 parts) of the solution of the Preparation Example 11 was mixed with 221 parts (solid content, 100 parts) of the emulsion obtained in Preparation Example 6, and the procedure of Comparative Example 1 was repeated to thereby obtain an O/W/O emulsion cream [Example 7].

Example 8

10 parts (solid content, 5 parts) of the solution of the Preparation Example 12 was mixed with 223 parts (solid content, 100 parts) of the emulsion obtained in Preparation Example 1, and the procedure of Comparative Example 1 was repeated to thereby obtain an O/W/O emulsion cream [Example 8].

Example 9

10 parts (solid content, 5 parts) of the solution of the Preparation Example 11 was mixed with 223 parts (solid content, 100 parts) of the emulsion obtained in Preparation Example 7, and the procedure of Comparative Example 1 was repeated to thereby obtain an O/W/O emulsion cream [Example 9]

Example 10

10 parts (solid content, 5 parts) of the solution of the Preparation Example 11 was mixed with 224 parts (solid content, 100 parts) of the emulsion obtained in Preparation Example 8, and the procedure of Comparative Example 1 was repeated to thereby obtain an O/W/O emulsion cream [Example 10].

Example 11

10 parts (solid content, 5 parts) of the solution of the Preparation Example 11 was mixed with 231 parts (solid content, 100 parts) of the emulsion obtained in Preparation Example 9, and the procedure of Comparative Example 1 was repeated to thereby obtain an O/W/O emulsion cream [Example 11].

[Evaluation Method]

The thus obtained O/W/O emulsion creams were evaluated for their evaporation residue, texture (spreadability), softness, tackiness, skin irritancy by the procedure as described below. The results are shown in Table 2.

Evaporation Residue

The evaporation residue was measured as in the case of the emulsion as described above.

Texture (Spreadability)

The spreadability was evaluated by placing 0.5 g of the cream on an artificial leather, and spreading the cream by moving one fingertip in circles (n=20). The spreadability of the Comparative Example 4 prepared by using a commercially available product was evaluated B, and the evaluation was conducted by using the Comparative Example 4 for the standard.

A: spreadability higher than Comparative Example 4
B: equivalent with Comparative Example 4
C: spreadability lower than Comparative Example 4

Softness

The Softness of the Comparative Example 4 prepared by using a commercially available product was evaluated B, and the evaluation was conducted by using the Comparative Example 4 for the standard.

A: lighter and softer texture than Comparative Example 4
B: equivalent with Comparative Example 4
C: inferior to Comparative Example 4

The evaluation was conducted by 10 people. The evaluation result of 6 or more people is shown in the table.

Tackiness

The tackiness of the Comparative Example 4 prepared by using a commercially available product was evaluated B, and the evaluation was conducted by using the Comparative Example 4 for the standard.

A: less oily and tacky than Comparative Example 4. Smooth with no tackiness.
B: equivalent with Comparative Example 4
C: inferior to Comparative Example 4

The evaluation was conducted by 10 people. The evaluation result of 6 or more people is shown in the table.

Skin Irritancy Test

Skin irritancy was evaluated by patch test (closed patch test) commonly used in confirming skin irritancy of cosmetic preparations.

A circular filter paper having a diameter of about 5 mm with the O/W/O emulsion cream, and this paper was adhered to upper arm by using an aluminum disk (Finn chamber) having the same diameter as the filter paper so that the filter paper was covered by the Finn chamber. The Finn chamber was secured by using a tape.

After 48 hours, the filter tape was peeled off the skin (patch removal), and the skin irritancy was evaluated by the skin reaction after 1 hour and 24 hours.

<Criteria>
No reaction: −
Slight erythema: ±
Erythema: +
Erythema and edema: ++
Erythema, edema, and small blisters: +++

The point given for each criterion was −:0, ±:0.5, +:1.0, ++:2.0, and +++:3.0. The point multiplied by the number of people showing the corresponding reaction was used as the score. The score of 1 hour after the patch removal (49 hour evaluation) and 24 hours after the patch removal (72 hour evaluation) were calculated. The score divided by the number of subjects and multiplied by 100 is irritancy index. The products with the irritancy index of up to 10 are safe products, 11 to 30 are acceptable products, and improvement is required for the products with the index in excess of 30.

Detailed results of the skin irritancy test are shown in Table 3.

Confirmation of Crosslinkability

Crosslinkability was confirmed by the actual progress of the crosslinking. 5 g of the emulsion was dried at 105° C. for 3 hours to obtain a rubbery oil. 1 g of this oil component was dissolved in 100 g of toluene, and after stirring the solution for 1 hour and filtration, the insoluble content was collected by filtration through a nylon filter cloth and dried at 105° C. for 1 hour. The more residue after the drying means higher degree of crosslinking. The value of 0.05% or higher was determined to indicate the crosslinking.

Increase in the filter cloth weight (g)/1 g=%  (*equation)

TABLE 2

| Content (parts by weight) | | Comparative Example 1 | 2 | 3 | 4 | 5 | 6 | 7 | Example 1 | 2 | 3 | 4 | 5 | 6 | 7 | 8 | 9 | 10 | 11 |
|---|---|---|---|---|---|---|---|---|---|---|---|---|---|---|---|---|---|---|---|
| (A) (Solid content) | Comparative Preparation Example 1 | 100 | | | | | | | | | | | | | | | | | |
| | 2 | | 100 | | | | | | | | | | | | | | | | |
| | 3 | | | 100 | | | | | | | | | | | | | | | |
| | 4 | | | | 100 | | | | | | | | | | | | | | |
| | Preparation Example 1 | | | | | 100 | | | | | | | | | | | | | |
| | 2 | | | | | | 100 | | | | | | | | | | | | |
| | 3 | | | | | | | 100 | | | | | | | | | | | |
| | 4 | | | | | | | | 100 | | | | | | | | | | |
| | 5 | | | | | | | | | 100 | | | | | | | | | |
| | 6 | | | | | | | | | | 100 | | | | | | | | |
| | 7 | | | | | | | | | | | 100 | | | | | | | |
| | 8 | | | | | | | | | | | | 100 | | | | | | |
| | 9 | | | | | | | | | | | | | 100 | | | | | |
| (B) (Solid content) | Preparation Example 11 | 5 | 20 | | | | | | 5 | 5 | 5 | 20 | 5 | 5 | 5 | 5 | 5 | | |
| | 12 | | | | | | | | | | | | | | | | | 5 | 5 |
| Isohexadecane | | 200 | 200 | 200 | 200 | 200 | 200 | 200 | 200 | 200 | 200 | 200 | 200 | 200 | 200 | 200 | 200 | 200 | 200 |
| KF-6105 (solid content) | | 200 | 200 | 200 | 200 | 200 | 200 | 200 | 200 | 200 | 200 | 200 | 200 | 200 | 200 | 200 | 200 | 200 | 200 |
| Confirmation of the crosslinkability (%) | | 0.10 | 0.19 | 0.02 | 0.02 | 0.01 | 0.01 | 0.02 | 0.12 | 0.09 | 0.12 | 0.25 | 0.10 | 0.20 | 0.14 | 0.15 | 0.15 | 0.13 | 0.19 |
| Results of evaluation | Evaporation residue (%) | 48 | 48 | 53 | 53 | 48 | 47 | 47 | 47 | 48 | 48 | 48 | 47 | 48 | 48 | 48 | 48 | 48 | 48 |
| | Texture (spreadability) | B | B | B | B | B | B | B | A | A | A | A | B | B | B | B | B | B | B |
| | Softness | A | A | B | B | B | B | B | A | A | A | A | A | A | A | A | A | A | A |
| | Tackiness | A | A | B | B | B | B | B | A | A | A | A | A | A | A | A | A | A | A |
| | Irritancy index (after 49 hours) | 15 | 12.5 | 0 | 0 | 17.5 | 5 | 12.5 | 0 | 2.5 | 2.5 | 0 | 2.5 | 5 | 2.5 | 2.5 | 0 | 0 | 2.5 |
| | Irritancy index (after 72 hours) | 5 | 0 | 0 | 0 | 7.5 | 0 | 0 | 0 | 0 | 0 | 0 | 0 | 0 | 0 | 0 | 0 | 0 | 0 |

KM-903: nonionic emulsion prepared by using a highly polymerized dimethicone diluted with a dimethicone having medium viscosity for the base oil (solid content, 60%) manufactured by Shin-Etsu Chemical Co., Ltd.
KM-910: nonionic emulsion prepared by using a highly polymerized dimethicone having a degree of polymerization higher than KM-903 diluted with a dimethicone having medium viscosity for the base oil (solid content, 60%) manufactured by Shin-Etsu Chemical Co., Ltd.
KF-6105: a polyglycerin-modified silicone oil manufactured by Shin-Etsu Chemical Co., Ltd.

As demonstrated by the results shown in Table 2, Comparative Examples 3 and 4 prepared by using KM-903 and KM-910 can not be regarded aqueous, and emulsification and dispersion of the silicone oil was required. This is commercially disadvantageous for the production of the silicone resin emulsion which is used as the main ingredient of a cosmetic preparation.

In contrast, the Examples using the silicone rubber emulsion of the present invention had the texture (spreadability) comparable to the O/W/O emulsion cream of Comparative Example 1. With regard to the softness, the Examples using the silicone rubber emulsion of the present invention had characteristic rubber elasticity compared to simple dimethicone gum, and therefore, they have light and soft texture. Tackiness is also greatly improved compared to the silicone oil, and the silicone rubber emulsions of the present invention are advantageous for cosmetic purpose compared to Comparative Examples 3 and 4 also in view of the tackiness.

Accordingly, performance comparable to those of conventional products is realized by the use of the silicone rubber emulsions of the present invention in producing the cosmetic products. Use of the silicone rubber emulsions of the present invention is also expected to bring the merits of rubber performance to the cosmetic products.

TABLE 3

| | | Evaluation time | | Evaluation Point − 0 | ± 0.5 | + 1.0 | ++ 2.0 | +++ 3.0 | Score | Irritancy index | Evaluation |
|---|---|---|---|---|---|---|---|---|---|---|---|
| Comparative Example | 1 | 49 h | No. of subjects | 15 | 4 | 1 | 0 | 0 | 3 | 15 | Acceptable product |
| | | | Score | 0 | 2 | 1 | 0 | 0 | | | |
| | | 72 h | No. of subjects | 18 | 2 | 0 | 0 | 0 | 1 | 5 | |
| | | | Score | 0 | 1 | 0 | 0 | 0 | | | |
| | 2 | 49 h | No. of subjects | 15 | 5 | 0 | 0 | 0 | 2.5 | 12.5 | Acceptable product |
| | | | Score | 0 | 2.5 | 0 | 0 | 0 | | | |
| | | 72 h | No. of subjects | 20 | 0 | 0 | 0 | 0 | 0 | 0 | |
| | | | Score | 0 | 0 | 0 | 0 | 0 | | | |
| | 3 | 49 h | No. of subjects | 20 | 0 | 0 | 0 | 0 | 0 | 0 | Safe product |
| | | | Score | 0 | 0 | 0 | 0 | 0 | | | |
| | | 72 h | No. of subjects | 20 | 0 | 0 | 0 | 0 | 0 | 0 | |
| | | | Score | 0 | 0 | 0 | 0 | 0 | | | |
| | 4 | 49 h | No. of subjects | 20 | 0 | 0 | 0 | 0 | 0 | 0 | Safe product |
| | | | Score | 0 | 0 | 0 | 0 | 0 | | | |
| | | 72 h | No. of subjects | 20 | 0 | 0 | 0 | 0 | 0 | 0 | |
| | | | Score | 0 | 0 | 0 | 0 | 0 | | | |
| | 5 | 49 h | No. of subjects | 13 | 7 | 0 | 0 | 0 | 3.5 | 17.5 | Acceptable product |
| | | | Score | 0 | 3.5 | 0 | 0 | 0 | | | |
| | | 72 h | No. of subjects | 15 | 3 | 0 | 0 | 0 | 1.5 | 7.5 | |
| | | | Score | 0 | 1.5 | 0 | 0 | 0 | | | |
| | 6 | 49 h | No. of subjects | 18 | 2 | 0 | 0 | 0 | 1 | 5 | Safe product |
| | | | Score | 0 | 1 | 0 | 0 | 0 | | | |
| | | 72 h | No. of subjects | 20 | 0 | 0 | 0 | 0 | 0 | 0 | |
| | | | Score | 0 | 0 | 0 | 0 | 0 | | | |
| | 7 | 49 h | No. of subjects | 15 | 5 | 0 | 0 | 0 | 2.5 | 12.5 | Acceptable product |
| | | | Score | 0 | 2.5 | 0 | 0 | 0 | | | |
| | | 72 h | No. of subjects | 20 | 0 | 0 | 0 | 0 | 0 | 0 | |
| | | | Score | 0 | 0 | 0 | 0 | 0 | | | |
| Example | 1 | 49 h | No. of subjects | 20 | 0 | 0 | 0 | 0 | 0 | 0 | Safe product |
| | | | Score | 0 | 0 | 0 | 0 | 0 | | | |
| | | 72 h | No. of subjects | 20 | 0 | 0 | 0 | 0 | 0 | 0 | |
| | | | Score | 0 | 0 | 0 | 0 | 0 | | | |
| | 2 | 49 h | No. of subjects | 19 | 1 | 0 | 0 | 0 | 0.5 | 2.5 | Safe product |
| | | | Score | 0 | 0.5 | 0 | 0 | 0 | | | |
| | | 72 h | No. of subjects | 20 | 0 | 0 | 0 | 0 | 0 | 0 | |
| | | | Score | 0 | 0 | 0 | 0 | 0 | | | |
| | 3 | 49 h | No. of subjects | 19 | 1 | 0 | 0 | 0 | 0.5 | 2.5 | Safe product |
| | | | Score | 0 | 0.5 | 0 | 0 | 0 | | | |
| | | 72 h | No. of subjects | 20 | 0 | 0 | 0 | 0 | 0 | 0 | |
| | | | Score | 0 | 0 | 0 | 0 | 0 | | | |
| | 4 | 49 h | No. of subjects | 20 | 0 | 0 | 0 | 0 | 0 | 0 | Safe product |
| | | | Score | 0 | 0 | 0 | 0 | 0 | | | |
| | | 72 h | No. of subjects | 20 | 0 | 0 | 0 | 0 | 0 | 0 | |
| | | | Score | 0 | 0 | 0 | 0 | 0 | | | |
| | 5 | 49 h | No. of subjects | 19 | 1 | 0 | 0 | 0 | 0.5 | 2.5 | Safe product |
| | | | Score | 0 | 0.5 | 0 | 0 | 0 | | | |
| | | 72 h | No. of subjects | 20 | 0 | 0 | 0 | 0 | 0 | 0 | |
| | | | Score | 0 | 0 | 0 | 0 | 0 | | | |
| | 6 | 49 h | No. of subjects | 18 | 2 | 0 | 0 | 0 | 1 | 5 | Safe product |
| | | | Score | 0 | 1 | 0 | 0 | 0 | | | |
| | | 72 h | No. of subjects | 20 | 0 | 0 | 0 | 0 | 0 | 0 | |
| | | | Score | 0 | 0 | 0 | 0 | 0 | | | |
| | 7 | 49 h | No. of subjects | 19 | 1 | 0 | 0 | 0 | 0.5 | 2.5 | Safe product |
| | | | Score | 0 | 0.5 | 0 | 0 | 0 | | | |
| | | 72 h | No. of subjects | 20 | 0 | 0 | 0 | 0 | 0 | 0 | |
| | | | Score | 0 | 0 | 0 | 0 | 0 | | | |

TABLE 3-continued

| | Evaluation time | | − 0 | ± 0.5 | + 1.0 | ++ 2.0 | +++ 3.0 | Score | Irritancy index | Evaluation |
|---|---|---|---|---|---|---|---|---|---|---|
| 8 | 49 h | No. of subjects | 19 | 1 | 0 | 0 | 0 | 0.5 | 2.5 | Safe product |
| | | Score | 0 | 0.5 | 0 | 0 | 0 | | | |
| | 72 h | No. of subjects | 20 | 0 | 0 | 0 | 0 | 0 | 0 | |
| | | Score | 0 | 0 | 0 | 0 | 0 | | | |
| 9 | 49 h | No. of subjects | 20 | 0 | 0 | 0 | 0 | 0 | 0 | Safe product |
| | | Score | 0 | 0 | 0 | 0 | 0 | | | |
| | 72 h | No. of subjects | 20 | 0 | 0 | 0 | 0 | 0 | 0 | |
| | | Score | 0 | 0 | 0 | 0 | 0 | | | |
| 10 | 49 h | No. of subjects | 20 | 0 | 0 | 0 | 0 | 0 | 0 | Safe product |
| | | Score | 0 | 0 | 0 | 0 | 0 | | | |
| | 72 h | No. of subjects | 20 | 0 | 0 | 0 | 0 | 0 | 0 | |
| | | Score | 0 | 0 | 0 | 0 | 0 | | | |
| 11 | 49 h | No. of subjects | 19 | 1 | 0 | 0 | 0 | 0.5 | 2.5 | Safe product |
| | | Score | 0 | 0.5 | 0 | 0 | 0 | | | |
| | 72 h | No. of subjects | 20 | 0 | 0 | 0 | 0 | 0 | 0 | |
| | | Score | 0 | 0 | 0 | 0 | 0 | | | |

As shown in Table 3, after 49 hours, Comparative Examples 1, 2, and 5 were at the level of the acceptable product with some irritancy and not the level of the safe product. In contrast, no reaction was observed in most people in the case of Examples 1 to 11, and this demonstrates dramatically reduced irritancy compared to Comparative Examples.

Japanese Patent Application No. 2012-043952 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A cosmetic preparation in the form of a foundation, an eyeliner, or a lipstick, said cosmetic preparation containing a crosslinkable silicone rubber emulsion comprising:
component (A) 100 parts by weight of a straight chain or branched organopolysiloxane containing at least two hydroxyl groups bonded to silicon atoms per molecule prepared by ring-opening polymerization of subcomponent (a1) a cyclic organosiloxane in the presence of subcomponent (a2) an alkoxysilane or its partial hydrolytic condensate or an α,ω-dihydroxy or dialkoxy siloxane oligomer, subcomponent (a3) at least one member selected from citric acid, lactic acid, and ascorbic acid, subcomponent (a4) an anionic surfactant and subcomponent (a5) 50 to 200 parts by weight of water in relation to 100 parts by weight of said cyclic organosiloxane; and
component (B) 0.5 to 20 parts by weight of a reaction product of an amino group-containing organoxysilane and an acid anhydride; and
at least one component selected from the group consisting of silicone oils, isoparaffin hydrocarbons, triglycerides, ester oils, lower alcohols, inorganic color pigments, inorganic white pigments, organic pigments, pearl agents, extender pigments, and organic powders.

2. The cosmetic preparation according to claim 1, wherein the straight chain or branched organopolysiloxane of component (A) is represented by the following general formula (1):

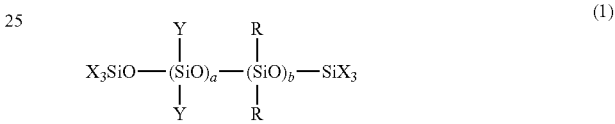

wherein R is independently an alkyl group containing 1 to 20 carbon atoms or an aryl group containing 6 to 20 carbon atoms; X is independently an alkyl group containing 1 to 20 carbon atoms, an aryl group containing 6 to 20 carbon atoms, an alkoxy group containing 1 to 20 carbon atoms, or hydroxyl group; Y is independently X or a group represented by —[O—Si(X)$_2$]$_c$—X, at least 2 of X and Y being hydroxyl group; letter a is an integer of 0 to 1,000; letter b is an integer of 100 to 10,000; and letter c is an integer of 1 to 1,000; with the proviso that each constitutional repeating unit may be randomly bonded.

3. The cosmetic preparation according to claim 1, wherein the amino group-containing organoxysilane of component (B) is the one represented by the following general formula (2):

wherein R is independently an alkyl group containing 1 to 20 carbon atoms or an aryl group containing 6 to 20 carbon atoms, A is an amino-containing group represented by the formula: —R$_2$(NHR$^1$)$_h$NHR$^2$ wherein R$^1$ is independently a divalent hydrocarbon group containing 1 to 6 carbon atoms, R$^2$ is R or hydrogen atom, and letter h is an integer of 0 to 6, and letter g is 0, 1, or 2, and the acid anhydride is a dicarboxylic acid anhydride.

4. The cosmetic preparation according to claim 1, wherein the catalyst for obtaining the component (A.) is citric acid.

5. The cosmetic preparation according to claim 1, wherein the anionic surfactant for obtaining the component (A) is at least one member selected from N-acylamino acid salt, N-acyltaurinate, aliphatic soap, and alkylphosphate salt.

* * * * *